(12) United States Patent
Luttermann et al.

(10) Patent No.: US 6,713,264 B2
(45) Date of Patent: Mar. 30, 2004

(54) PROCESS AND DEVICE FOR THE SCREENING OF MOLECULES WITH REGARD TO THEIR INDIVIDUAL BINDING BEHAVIOUR TOWARDS AT LEAST ONE GIVEN LIGAND

(75) Inventors: Klaus Luttermann, Neunkirchen (DE); Edgar Diessel, Köln (DE); Winfried Kosch, Wiesbaden (DE); Walter Weichel, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 08/891,778

(22) Filed: Jul. 14, 1997

(65) Prior Publication Data

US 2002/0137091 A1 Sep. 26, 2002

(30) Foreign Application Priority Data

Jul. 19, 1996 (DE) .......................... 196 29 141

(51) Int. Cl.⁷ .................... G01N 33/53; G01N 21/64
(52) U.S. Cl. ................ 435/7.1; 435/30; 435/34; 435/286.1; 435/287.1; 435/287.3; 435/288.5; 435/808; 435/888.7; 422/82.08; 422/82.05; 356/36; 356/38; 356/337; 356/338; 356/341; 356/343
(58) Field of Search ................ 435/7.1, 286.1, 435/808, 888.7, 287.1, 287.3, 30, 34, 288.5; 422/82.08, 82.05; 356/36, 38, 337, 338, 341, 343

(56) References Cited

U.S. PATENT DOCUMENTS

| 4,729,949 A | | 3/1988 | Weinreb et al. | |
|---|---|---|---|---|
| 4,907,158 A | | 3/1990 | Kettler et al. | ................. 700/58 |
| 5,073,495 A | * | 12/1991 | Anderson | ................. 435/284 |
| 5,114,854 A | | 5/1992 | Bertholdt | ................. 435/30 |
| 5,480,804 A | * | 1/1996 | Niwa et al. | ................. 435/286.1 |
| 5,760,900 A | * | 6/1998 | Ito et al. | ................. 356/338 |
| 6,225,625 B1 | * | 5/2001 | Pirrung et al. | ................. 250/302 |

FOREIGN PATENT DOCUMENTS

| DE | 4414940 | | 11/1995 | |
|---|---|---|---|---|
| EP | 0 539 888 A1 | | 10/1992 | |
| EP | 539 888 A1 | * | 5/1993 | ........... C12M/1/34 |
| EP | 0539888 | | 5/1996 | |
| GB | 2211111 | | 6/1989 | |
| JP | 61001378 | | 7/1986 | |
| JP | 406167453 | * | 6/1996 | .......... G01N/21/78 |
| JP | 230912 | | 8/2000 | |
| JP | 231165 | | 8/2000 | |
| WO | 8805908 | | 8/1988 | |
| WO | 88/05908 | * | 8/1988 | .......... G01N/15/14 |
| WO | 91/19199 | * | 12/1991 | |

* cited by examiner

*Primary Examiner*—Bennett Celsa
(74) *Attorney, Agent, or Firm*—Norris McLaughlin & Marcus

(57) ABSTRACT

The process is used for the screening of molecules from molecule libraries with regard to their individual binding behavior towards at least one given ligand. For this purpose the ligands labelled with a fluorescent dye are mixed with the molecule library which is in the form of a suspension. The mixture is plated out on a two-dimensional substrate (2) after the excess, unbound ligands have been washed out. Then the local fluorescence intensities on the substrate are electro-optically identified in a fluorescence microscope (5) and electronically discriminated in accordance with given selection criteria. The objects selected and localised in this way are then sequentially positioned exactly by a displacement, the coordinates of which are controlled by the image calculator, between the substrate (2) and a separation actuator (20, 21) and are spatially separated from the substrate (2) by the separation actuator (20, 21).

6 Claims, 4 Drawing Sheets

PROCESS AND DEVICE FOR THE SCREENING OF MOLECULES WITH REGARD TO THEIR INDIVIDUAL BINDING BEHAVIOUR TOWARDS AT LEAST ONE GIVEN LIGAND

The invention relates to a process and a device for an optimised selection of molecules from molecule libraries with regard to their binding behaviour towards one or more given target molecules, which for the first time allows a very great variety of molecules to be investigated, provides information on individual binding events and allows a sparing selection of the molecules being selected.

The molecule libraries forming the basis for the selection process according to the invention are generated by chemical methods (combinatorial chemistry) or by biotechnological methods within the field of Applied Molecular Evolution (AME). In this connection combinatorial chemistry utilises all manner of chemical reactions for the construction of molecule libraries, whereas AME produces a large population of different biopolymers by means of mutation strategies. The efficient selection of molecules or biopolymers binding to a specific target is a substantial element in the discovery of new pharmaceutical active ingredients (pilot structures) and therefore of great importance.

In principle, processes within the field of AME for protein design are known and established. The evolutive strategy was applied, for example, in the discovery of peptide ligands (O'Nell et al., Prot. 14, 509 (1992) and in the development of customised high-affinity antibodies (Breitling et al., Gene 104, 147 (1991), Clackson et al., Nature 352, 624 (1991), Marks et al., J. Mol. Biol. 222, 581 (1991), Persson, Proc. Natl. Acad. Sci. USA 88, 2432 (1991)). Antibody-engineering in particular is a promising concept of applied evolutive biotechnology. Owing to their highly selective binding properties, antibodies are important reagents in research, diagnostics and therapy (Plückthun, J. Anal. Chem. 337, 13 (1990), Plückthun, Biotechnology 9, 545 (1991), Little et al., Biotech. Adv. Vol. 12, 539 (1994)). Apart from the formation of molecule libraries by AME, the use primarily of combinatorial chemistry has recently become established. This exploits a variety of chemical reactions for the synthesis of the library on solid supports such as, for example, polymer beads (D. J. Ecker, S. T. Crooke, Biotechnology, 1995, 13, 351; R. M. J. Liskamp, Angew. Chemie, 1994, 106, 661; T. Carell, E. A. Winter, A. Bashir-Hashemi, J. Rebek, Angew. Chemie, 1994, 106, 2159; J. W. Metzger, K. -H. Wiesmüller, V. Gnau, J. Brünjes, G. Jung, Angew. Chemie, 1993, 105, 901). An example which may be mentioned here is the solid-phase synthesis of benzodiaze-pines by Hobbs, De Witt et al. (Proc. Natl. Acad. Sci., USA, 1993, 60, 6909).

A condition of the process according to the invention is that the molecule libraries must be based on supports. The measurement of a large number of like molecules is thereby made possible and the individual binding behaviour can be adequately characterised in this way. Examples of a suitable support-based system are bacteria within the field of AME or polymer beads within the field of combinatorial chemistry.

Processes for the production of protein libraries on *E. coli* bacteria are known in the literature (Hofnung, Meth. Enzymol. 134, 77 (1991), Klauser et al., EMBO J., 9, 1991 (1990), Fuchs et al., Biotechnology 9, 1369 (1991), Francisco et al., Proc. Natl. Acad. Sci. USA 89, 2713 (1992), Pugsley, Proc. Natl. Acad. Sci. USA 89, 12058 (1992)). In addition, the expression on a phage surface is described (Hoogenboom et al., Immunolog. Reviews 130, 41 (1992)), which is irrelevant to the process according to this invention owing to the phage size (<<1 $\mu$m).

Technical solutions for selection processes for the separation of cells from a large number (>$10^6$) are commercially available in the FACS (Fluorescence-Activated Cell Sorter) and MACS (Magnetic Activated Cell Sorter).

Fluorescence-activated cell sorting uses electrostatic principles for the spatial separation. A commercial FACS (Becton & Dickinson: FACStar Plus) is capable of sequentially processing about $10^8$ cells per day. But here it has to be taken into account that the useful sorting rate is significantly less than 100%. In very rare events in a cell population, however, high throughputs of about $10^9$ are desirable.

Compared with the process according to the invention, in the case of FACS the sorting process moreover takes place directly after the measuring process, so that in the event of a subsequent correction to the threshold values for affinities, the entire sorting process has to be repeated. This is accompanied by a further mechanical stress on the molecule support or on the bacteria.

The MACS sorting process utilises the binding of the relevant cells to magnetic beads. In the separation step, the cells labelled in this manner are retained in the MACS column by an inhomogeneous magnetic field, while the unlabelled cells pass unimpeded through the column. By this process, however, it is possible only to distinguish between magnetic and non-magnetic cells. MACS accordingly permits a rapid processing of large populations, but no information about individual binding events can be obtained.

The separation of beads in combinatorial chemistry is conventionally carried out by a manual method.

This invention is based on the object of developing a process whereby, out of a large number ($10^9$) of molecules from a molecule library, it is possible within 24 hours to detect and separate individual objects, which are identified by their particular binding affinity to one or more given ligands. The vitality of the bacterial population is to be preserved for the subsequent propagation (amplification) of bacteria within the field of AME.

This object is fulfilled according to the invention by a process comprising the following steps.

a) The ligands to be bound are labelled with a fluorescent dye and mixed with the molecule library which is in the form of a suspension.

b) The excess ligands not bound to molecules in the molecule library are then washed out and removed.

c) This mixture is plated out on a two-dimensional substrate.

d) The substrate thus coated is placed under a fluorescence microscope. The local fluorescence intensities observed on the substrate are then identified electrooptically and by means of a CCD camera are digitally identified in the form of a total image or stepwise in the form of partial images and are electronically discriminated in accordance with given selection criteria in the form of threshold values, and the objects situated on the substrate, which are characterised by a high binding affinity of the ligands for molecules of the molecule library and thereby fulfill the selection criteria, are identified and localised by storage in an image calculator.

e) The objects thus selected are then positioned sequentially at the operating point of a separation actuator by a relative displacement—the coordinates of which are controlled by the image calculator—between the substrate and a separation actuator, are removed from the substrate and separately deposited locally.

The identification and separation of molecules from a library of biomolecules in accordance with the above procedure assumes that these molecules are present in sufficient number on the surface of a suitable biological cell. To this end, the genetic information for a biomolecule is funnelled into a large population of microorganisms, which thereupon synthesise the biomolecule. The processes which include this control of a microorganism for biochemical synthesis are collectively termed expression systems. The diversity of the library arises as a result of the diversity of mutants of the funnelled information. Here complexities of $>10^9$ can be produced.

The electrooptical identification of the local fluorescence intensities on the substrate is advantageously carried out in the form of a total image or stepwise in the form of partial images by means of a CCD camera. The total image or the partial images, optionally after a data reduction, are then passed to the image calculator for storage and for further processing by image analysis and evaluation in accordance with the given selection criteria.

Alternatively, the electrooptical identification of the local fluorescence intensities on the substrate can also be carried out by means of a laser scanner, the output signals of which are evaluated electronically in accordance with the given selection criteria and in combination with the associated local coordinates are passed to the image calculator.

E. coli bacteria are preferably used as the bacterial expression system in the production of a biomolecule library.

For the production of a peptide library and/or protein library, the specific bacterial expression system particularly preferably used comprises E. coli bacteria which express variations of LamB transmembrane proteins through genetic manipulation.

In addition to an optimised selection and separation of molecules from a molecule library formed from microorganisms, the process also relates to the selection and separation of molecules from a molecule library produced by chemical methods. In combinatorial chemistry, molecule libraries are produced on a solid phase by means of chemical methods (reactions). The diversity of the library arises as a result of using a variety of reactions and reagents. These molecule libraries are advantageously produced on polymer beads. Plastics polystyrene or polyacrylamide beads having a diameter of from 50 μm to 200 μm are preferably used as polymeric supports.

To render possible the investigation of several ligands simultaneously, different ligands are usefully labelled with different fluorescent dyes. The selection criteria for the different ligands are given in the form of a list of the threshold values for the fluorescence intensities of different colours.

A further development of the process according to the invention consists in the proteins supporting the molecule library on the bacteria or the compounds obtained from combinatorial chemistry on the polymer beads being labelled with a further fluorescent dye and the fluorescence intensity of the binding sites being taken into account as an additional selection criterion in the image analysis.

In this case, the ratio of the fluorescence intensity characteristic for the ligand to the fluorescence intensity characteristic for the binding site can be used in the image analysis as a decisive selection criterion for the binding affinity.

The device for carrying out the process according to the invention comprises an inverse fluorescence microscope and a moving stage for holding a support together with the plated-out object in suspension, and at least one light source for exciting the fluorescence and according to the invention is characterised in that a) an electrooptical scanning device, consisting of a CCD camera or of a laser scanner, for the identification of the local fluorescence intensities of the suspensions of bacteria plated out on the substrate is provided, which device is connected to an image calculator for the further processing and storage of the fluorescent image information, b) a separation actuator for the transfer of the selected objects is arranged above the moving stage, c) and the image calculator controls the positioning of the moving stage relative to the separation actuator.

The separation actuator advantageously comprises a lowerable microcapillary incorporated in a micromanipulator.

In a preferred embodiment, the light which excites the fluorescence is passed to the substrate across at least one optical waveguide separated from the path of the beams from the microscope. For this purpose, two different lasers having different wavelengths, which can be enclosed in the same optical waveguide, are provided in order to excite the fluorescence.

To avoid artefacts, the fluorescence microscope including the illumination device and the microcapillary are incorporated into a climatic chamber, which is cooled to temperatures of between 1° C. and 10° C. by means of a current of air saturated with water vapour. These artefacts may be, for example, the propagation of the bacteria, shrinkage of the agarose substrate and temperature fluctuations.

The chief advantage of the process described is the individual quantification and individual selection of binding complexes accompanied by a high throughput of the binding events to be analysed. This leads to a considerable reduction in time and costs. Moreover, in the case of biological objects the vitality of the selected cells is ensured.

The process for characterising molecular libraries can be used within the framework of fundamental scientific investigations. A possible industrial use is the search for pilot structures for new pharmaceuticals. By means of the process according to the invention, with the establishment of suitable libraries of antibodies a pharmacological individual therapy is possible whereby a medicine customised for the individual patient can be found, isolated and propagated in one day.

The invention is explained in more detail below with the aid of drawings and Examples.

Figure 4:
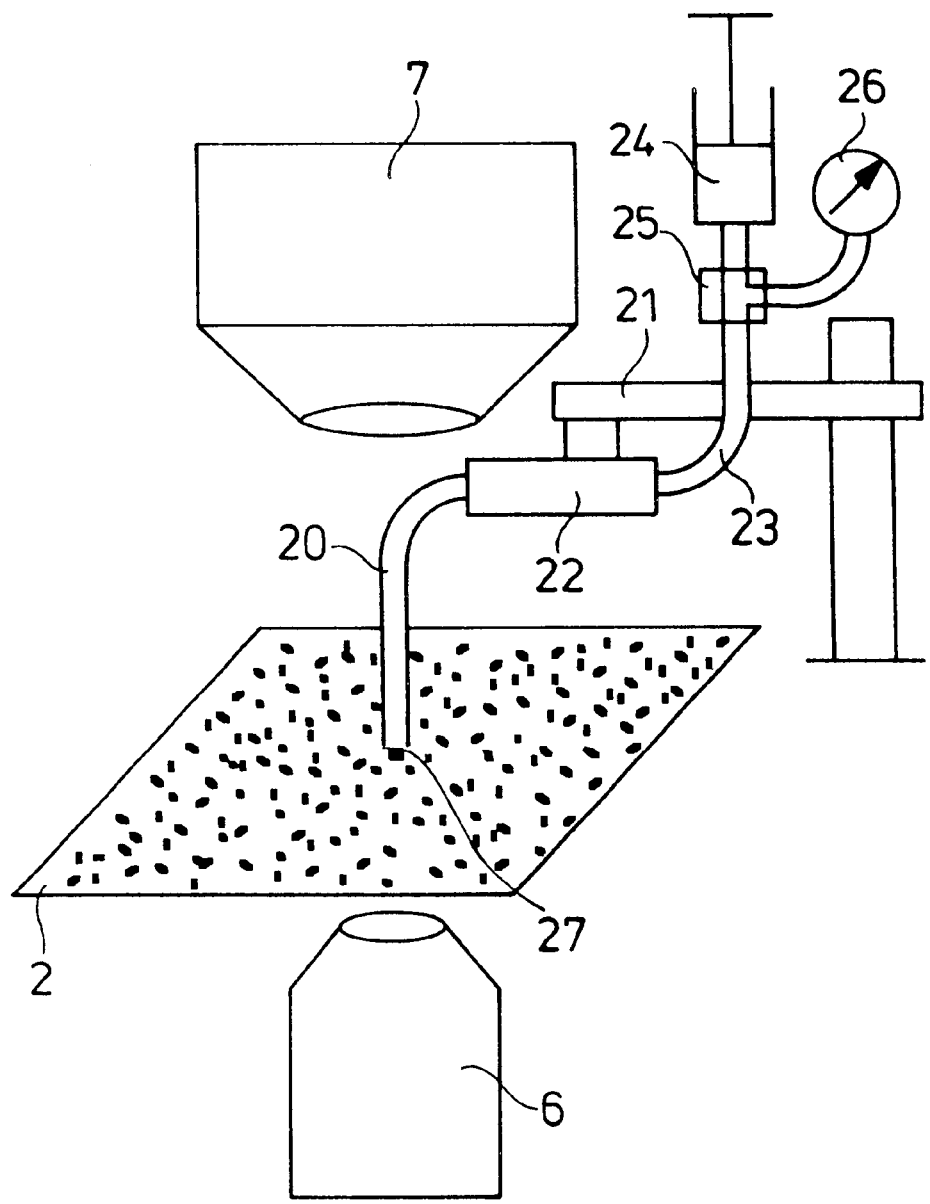

FIG. 4 shows a separation actuator for the transfer (separation) of the selected characteristic objects The carrying out of the process of selection and separation according to the invention for the selection and separation of molecules having high binding affinity to a target molecule requires the provision of a suitable molecule library and a target molecule, which is henceforth referred to as a ligand. This is described below using the example of a peptide library. Here E. coli bacteria which express variations of LamB transmembrane proteins through genetic manipulation are used for the presentation of this biomolecule library. The ligand chosen is the acetylcholine receptor. In contrast to the widely-used phage method, the bacterial system, owing to the multiplicity of similar binding events on the surface of the bacteria, affords the advantage that a single examination of the interaction between peptide-supporting cell and receptor may be carried out. A similar procedure using phages is ruled out owing to the small size of the phage particles.

Ligands labelled with a fluorescent dye are mixed with the peptide-supporting bacteria. For this purpose, for example, the dye ®Cy5 (product of the firm Biological Detection Systems) is used, which is excited at 650 nm and emits at 670 nm. Owing to the long-wave excitation, the fluorescence signal can be detected largely free from autofluorescence. As the number of peptides on the surface of the bacteria is not constant, a molecule section, which is the same for all peptides on all bacteria, is specifically labelled with a further dye, in order to obtain from its fluorescence signal a measure of the number of binding sites. A measure of the binding affinity of the complex can be obtained from the ratio of the two fluorescence intensities. The second fluorescent dye employed is ®FITC (product of the firm Molecular Probes), which is excited at 490 nm and emits at 520 nm. With these spectral characteristics, the two fluorescence signals are measured without mutual interaction.

After the ligand labelled with dye has been mixed with the suspension of bacteria (incubation), the bacteria are washed by being centrifuged off and subsequently dispersed in pure buffer solution. As a result, only fluorescence dyes situated exclusively on the surface of the bacteria remain behind in the dispersion of bacteria.

Figure 1:
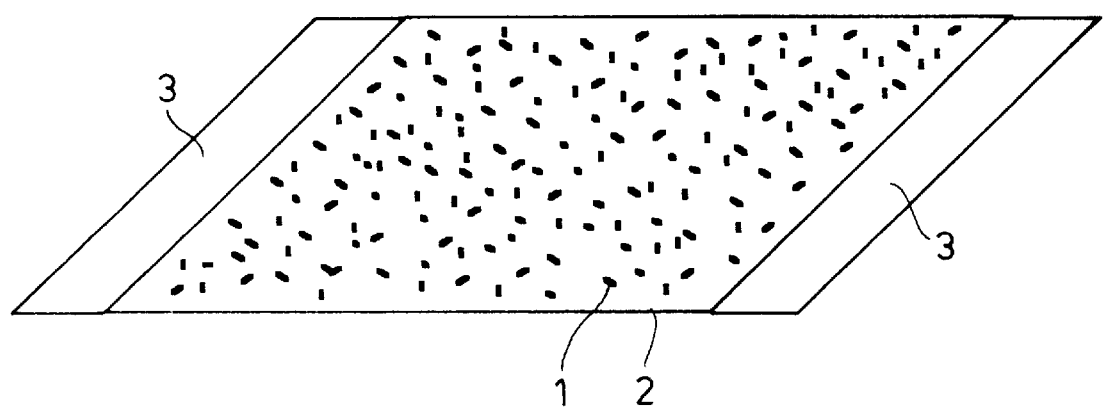
FIG. 1 shows a planar substrate with the plated-out bacterial suspension

This dispersion of bacteria 1 is then plated out by means of a spatula onto an agarose surface situated on a planar substrate 2 (see FIG. 1). The agarose surface is divided in such a way that in each edge region there are separate zones 3, on which the separated bacteria later come to lie. These agarose surfaces 3 which, in contrast to the substrate, contain nutrients, can be separated from the substrate 2 by peeling off. A surface covering density of 10% is aimed for, in order subsequently to achieve efficient measuring of the fluorescence intensities of the bacteria placed in a single plane on the substrate. For a population of $10^9$ species, the resulting total area is 250 cm$^2$.

Figure 2:
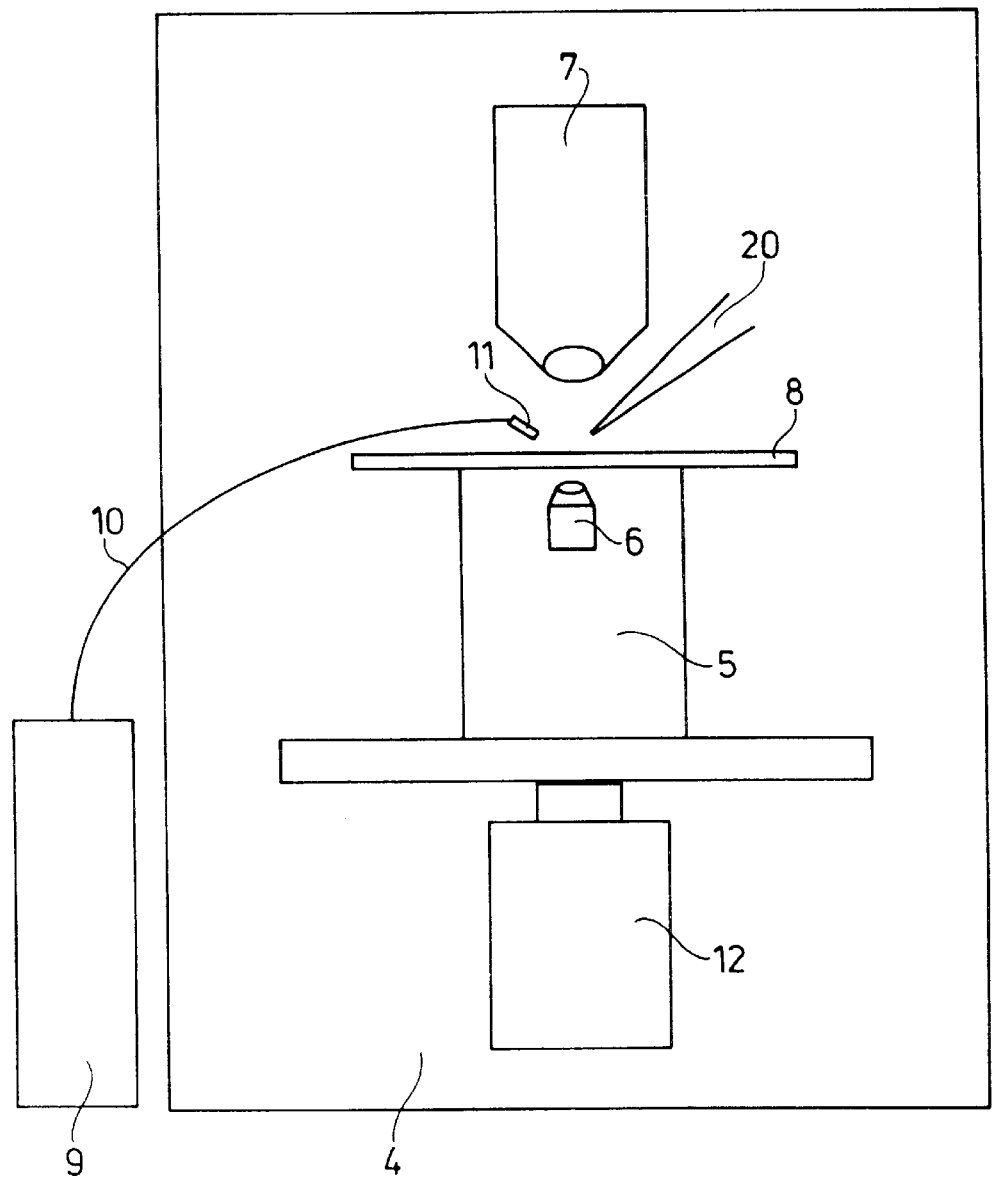
FIG. 2 shows a diagram of a selection apparatus based on a CCD camera

FIG. 2 shows a diagram of the construction of the entire selection machine. The technical tasks involve taking fluorescence recordings and the subsequent separation of bacteria, which are distinguished by predetermined specific binding properties. Artefacts such as, for example, bacterial propagation, are to be excluded during the measuring process. This is brought about by a climatic chamber 4, which is cooled by a current of air at 4° C. saturated with water vapour. The heart of the machine consists of an inverse microscope 5. The image objective 6, the illumination condenser 7 and the moving stage 8, upon which the substrate 2 is held, are parts of the microscope. The light source used for the fluorescence spectroscopy is a laser module 9, which consists of two lasers and an optical arrangement which encloses the two laser beams via electronic shutters alternating in an optical waveguide 10 having a core diameter of 200 µm. A Kr ionic gas laser operated at a wavelength of 647 nm with a power of 500 mW is used for the excitation of the ligand fluorophore. The second light source for the excitation of the second fluorophore at the binding site on the bacterium is an Ar ionic gas laser adjusted to an emission at 488 nm and to a comparable power. A microoptic 11, which produces a luminous spot of 1.5 mm in diameter on the sample, is attached to the end of the optical fibre. The external laser excitation avoids scattered light and background fluorescence in the image objective 6. The high laser intensity permits exposure times in the range of 0.1 to 1 s per exposure. The fluorescent light emitted from the substrate 2 is detected by a cooled CCD camera 12. The number of pixels of this fluorescent image is 1000*1018, so that calculations can be made at a microscope magnification with a resolution of 1.2 µm. This value is coordinated with the bacterial size which lies within this range. In front of the camera 12 there is an emission filter coordinated with the two fluorophores. The focussing position of the objective 6 is adjusted by a motor-operated device (not shown in the Figure). A device for this focussing adjustment, which operates by a rear reflection of a surface, is described, for example, in G. Bouwhuis et al., p 75 ff., A. Hilger Ltd (UK/USA), 1985.

For effective image analysis, a data reduction is carried out in the plane of the frame grabber board of the CCD camera. The software in this case is designed for the detection of binding events anticipated as being rare. With the aid of Look-Up Tables (LUT), it is first of all checked whether, on the fluorescence recording of the labelled ligands, there are fluorescence signals above a selected threshold value $S_1$. If the proof is positive, the second fluorescence recording of the binding site fluorophore is taken. After the quotient of the two signals has been calculated, the pixel coordinates together with the quotient are stored in the image calculator only for cases where these quotients are above a selected threshold value $S_2$. To this end, the lines which contain the significant pixels are ascertained on the frame grabber board. In the second step, these lines are transferred to the image calculator and there a search is made for the significant pixels. Alternatively, the entire image analysis of the ligand image can be carried out exclusively in the image calculator in accordance with the given selection criteria, that is, the detection and localisation of the objects situated on the substrate 2 and characterised by a high binding affinity of the ligands for the molecules of the molecule library. By "high binding affinity" it is meant that the fluorescence intensities of these objects fulfil the selection criteria with regard to the above-mentioned threshold value $S_2$.

The entire process of fluorescence recordings is based on the following time consideration. At a tenfold magnification, the CCD camera detects an image aperture of 1.2*1.2 mm. For a surface requirement for all bacteria of 2.5*$10^4$ mm$^2$, 17400 frames must be recorded. For the analysis of a double fluorescence, a cycle time of 4.1 s is estimated per frame, which includes an exposure time of 1 s in each case. An allowance is made here for the time for the movement of the moving stage. This results in a total time for the complete exposure process of 20 h, or a processing throughput of $10^9$ per day, and therefore meets the standard.

Figure 3:
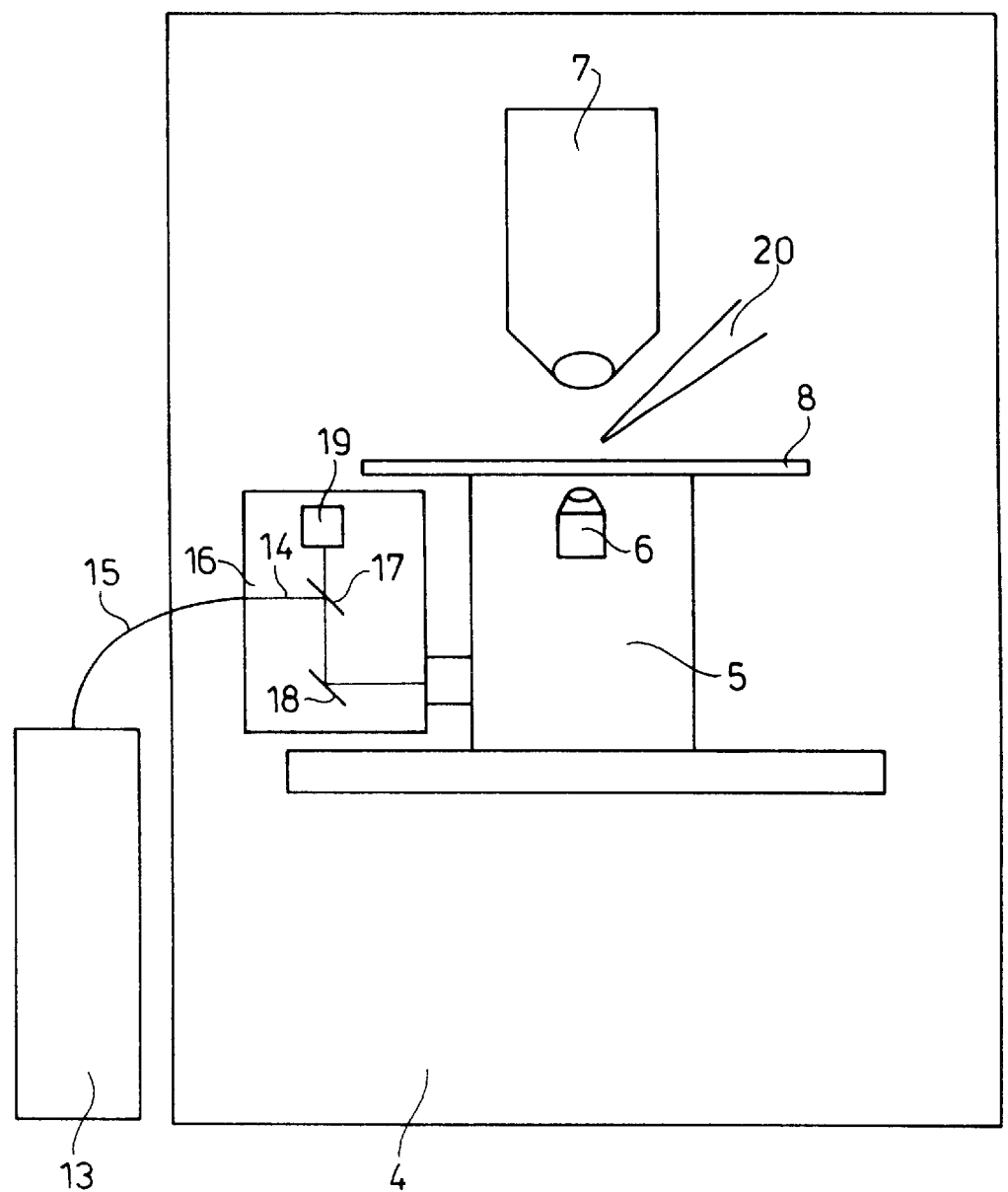
FIG. 3 shows a diagram of a selection apparatus based on a laser scanner

As an alternative to the detection of fluorescing objects by means of a simultaneous fluorescence excitation of the entire field of view of the microscope and to the parallel detection of the fluorescent image with a CCD camera, a spot scanning fluorescence excitation using a laser-scan device may be selected. A construction of this type is shown diagrammatically in FIG. 3. The laser beam 14 produced from an Ar—Kr laser 13 having an output of 20 mW is enclosed by a monomode optical fibre 15 in an optical module 16. In this module 16 the exciting laser beam is passed via a dichroitic beam splitter 17 to an x-y mirror 18. The computer-controlled mirror 18 deflects the laser beam in such a way that the laser beam focussed through the objective 6 onto a point scans the plane of the sample in the x-y direction. The local coordinates of a fluorescing object are stored here via the controlling variables of the deflecting mirror. These variables are unambiguously associated with the x-y location of the laser beam on the sample surface. This coordination is utilised in commercially available scanners (for example, Leica TCS4D Scanner, Leica Lasertechnik GmbH, Heidelberg, Germany). The fluorescent light from the sample reaches the beam splitter 17 via the objective 6 and the deflecting mirror 18 and is transmitted there in the opposite direction to the exciting beam. The fluorescent light is detected behind the beam splitter 17 in a detection module 19. This module comprises a pinhole, whereby fluorescent light outside the plane of focus can be suppressed, two photomultipliers for the two fluorescence emissions of FITC and Cy5 and the corresponding chromatic filters. During the scanning process the fluorescence intensities of the labelled ligands and of the binding site fluorophore are simultaneously measured and divided one into the other, so that no separate second fluorescence recording is necessary. The quotient can therefore be discriminated online from a threshold value $S_2$ and, on completion of the scan, only the coordinates and intensities of the pixels having intensities above the set threshold value $S_2$ are present in the working memory of the controlling and analysing computer. As an alternative thereto, however, the total image can be processed on the analysing computer on completion of the scanning process, in order optionally to be discriminated later using different threshold values.

In the case of a scanning surface of $2.5*10^4$ mm$^2$, a field of view of 1 mm$^2$ in size and a scanning time of 1.1 s (Zeiss-LSM) per field of view, the resulting total time for the complete fluorescence analysis is 11 hours, allowing for the movement of the stage bearing the sample.

Following the complete scanning process by the CCD camera or by the laser scanner, the memory of the image calculator contains a list of local coordinates of bacteria having specific binding properties, with the aid of which the separation of the bacteria is undertaken. The number of bacteria to be separated may optionally be limited on the basis of the list.

After the screening has been concluded and the local coordinates of the bacteria to be separated are known, the latter have to be removed from the substrate by means of a suitable separation actuator and deposited on a target substrate. A separation actuator based on a microcapillary 20 is used for this purpose. Separation actuators of this kind are known in principle from the patch clamp technique.

The apparatus for the transfer process is shown diagrammatically in FIG. 4. The microcapillary 20 can be moved by means of a micromanipulator 21 and, in accordance with the list of coordinates in the image calculator, is brought in turn to the bacteria to be selected and is accurately positioned above them. The image calculator therefore functions as a control calculator for the micromanipulator 21 for the seeking out and for the positioning of the microcapillary 20 at the site of the selected bacteria. The selected bacterium is then sucked from the surface of the substrate by the microcapillary 20 and again placed on a target substrate. Here the edge zones 3 on the substrate 2, which are prepared using agar surfaces or agarose surfaces, serve as the target substrate. Because the aim is to manipulate individual bacteria at a high covering density, the diameter of the microcapillary is accommodated to the size of the objects and accordingly measures between 2 and 20 $\mu$m.

Microcapillaries made of a special glass, which have been produced in the melted state by a drawing process, are preferably used for the transfer of the bacteria. Borosilicate glass tubes (firm Hilgenberg, Malsfeld, Germany) having an original diameter of 1.6 mm are used for the experiments to be described. In a three-step drawing process employing a commercially available pipette drawing device (DMZ Universalpuller, firm Zeitz-Instrumente, Munich, Germany), capillaries are produced in the shape of a cylindrical pipette (that is, not drawn out to a point) having a diameter at the opening of about 6 $\mu$m at the melted end. On the other side the original diameter remains unchanged. This pipette shape has proved useful for the reproducibility of the transfer process, in particular the rinsing process.

As may be seen from FIG. 4, the microcapillary 20 is held in a clamping device 22 attached to the micromanipulator 21, which can be positioned three-dimensionally in the $\mu$m range and the movement of which is controlled by the image calculator. Manipulators of this type are available commercially. The microcapillary is connected via a tube 23 to a syringe 24, by means of which the internal pressure in the capillary is adjusted. The pressure is determined by a pressure gauge 26 via a three-way tap 25. Both the micromanipulator 21 and the syringe 24 are operated by remote control using pulse motors (not shown here) and are guided by the image calculator.

The separation procedure as an interactive process is described below. It may however also proceed fully automatically under the control of a computer.

The entire process of the suction and separation of a bacterium (picking process) is based on visual control, which is rendered possible by observation at a 40-fold magnification in phase contrast. The only parts of the microscope shown here are the objective 6 and the illumination condenser 7. In view of the required operating distance of about 22 mm from the condenser 7 to the object, the microcapillaries 20 are heated to above the softening point and are bent in such a way that they form an angle of almost 90° and can therefore be compactly positioned under the condenser. In this way the observation of the transfer process can take place undisturbed. For a high spatial resolution of the transfer process within the dimensions of the pipette diameter (here 6 $\mu$m), it is crucial that the pipette should make vertical contact with the object being picked. Consequently no water film, which could affect surrounding objects during the transfer process, is formed between the capillary wall and the agar substrate. In preparation for the picking, a buffer solution is sucked into the capillary 20 from a storage jar by means of a vacuum. Here it is sufficient that only the tapered part of the capillary be filled with the buffer solution.

The object to be picked or the bacterium 27 to be separated from the substrate 2 is then positioned below the capillary 20 by the movement of the moving stage 8 of the microscope, the coordinates of the movement being controlled by the image calculator. Here the internal pressure in the capillary is adjusted to −300 mbar relative to ambient pressure. While simultaneously being observed through the microscope, the capillary 20 is placed directly onto the agarose substrate 2 above the bacterium 27 to be picked. The microcapillary 20 is then raised by the height adjustment on the micromanipulator and as a result the vacant substrate surface remains behind in the microscope image. To rinse out the bacterium 27, either the microcapillary 20 or the moving stage 8 are moved to an appropriate position on the target substrate. Here the internal pressure is increased to +100 mbar. While the capillary is being placed on the target substrate (in this case, the edge zone 3 on the substrate 2), the rinsing out process takes place. After the capillary 20 has been lifted again from the target substrate 3, the rinsed bacterium is once more visible in the phase contrast image of the microscope.

In each of four examples, 10 bacteria were transferred from a main growth medium to a target substrate, which contained nutrients. After a growth period of several days, colonies formed from the individual bacteria in 50 to 60% of the cases. In a test of the vitality rate of the parent population, a value of 60% was determined, so that on the basis of this the transfer process can be regarded as very sparing. Alternatively, the bacteria can be placed in a liquid, for example, PBS buffer. This liquid can be placed in the depressions (wells) of commercially available 96 or 384 microtitre plates.

In addition to the picking and rinsing process which take place in immediate succession, several bacteria were also picked one after the other and correspondingly rinsed one after the other. This procedure is comparatively time-saving, as the paths between the objects to be sorted can be optimised and moreover the adjustment of pressure in the capillary needs to be made only once in each case. The advantage of the use of bacteria is the simple amplification by regular growth. Furthermore, from individually sorted bacteria it is possible by means of the Polymerase Chain Reaction (PCR) to amplify the gene sequences responsible for the specific character of those bacteria.

The entire process of selection and separation is described once more in outline below. The first step consists in the preparation of samples. Fluorescence-labelled ligands are mixed with the dispersion of bacteria. After this incubation step, the bacteria are washed by being centrifuged off with a buffer solution. This dispersion of bacteria is then placed on a planar agarose substrate 2. The substrate 2 is placed on the moving stage 8 of the inverse microscope 5. The second step of the selection process consists now in carrying out the fluorescence recordings. Initially, the moving stage 8 is positioned so that the upper left corner of the region of the sample to be scanned comes to lie in the image region of the microscope. The subsequent movements of the stage follow a meandering course which covers the entire sample surface. For the fluorescence recording, the laser beam is released via a shutter in order to excite the ligand fluorescence, and is enclosed in the optical fibre 10 in order to irradiate the sample. The recording mode of the CCD camera 12 is then started. At the end of the exposure time, the shutter of the laser module 9 is closed. On the frame grabber board of the CCD camera 12, the fluorescent image is scanned for pixels above the selected threshold value $S_1$. If no pixels are found, the stage is moved to the next position and the image-recording process is repeated in the manner described. If in the course of the analysis pixels above the threshold value are detected, then another fluorescence recording of the binding site fluorophore is carried out with the stage in the same position. For this purpose, the shutter of the laser module 9 is opened for the second laser and the image recording by the CCD camera 12 is started. On conclusion of the image recording, the shutter is again closed. The quotient of the image of the ligand fluorescence and the image of the binding site fluorescence is again obtained in the plane of the frame grabber board. From the quotient image, those pixels which are above the threshold value $S_2$ are then detected. The pixel coordinates and the associated quotient values are determined in the image calculator, which stores this information in a data file. On conclusion of this software analysis, the stage is moved to the next position and the scanning process is repeated cyclically until the entire sample has been characterised by fluorescence spectroscopy.

When the scanning process has been concluded, the separation of the bacteria is carried out in the third step. For this purpose, with the aid of the pick lists stored in the image calculator, the moving stage is moved gradually to the bacteria which are to be separated. The microcapillary 20 is then lowered onto the selected bacterium 27 and sucked in by a vacuum. After the capillary 20 has again been raised from the substrate 2, the moving stage 8 moves to the free target substrate surfaces 3, where the bacterium 27 is deposited. To this end, the capillary 20 is lowered onto the substrate 3 and the bacterium 27 is rinsed out by the excess pressure established in the capillary 20. This procedure is repeated until the entire pick list has been processed. The positions of the examined bacteria are recorded in the image calculator so as to ensure a later allocation. On conclusion of the transfer of the bacteria, the target substrate 3 together with the separated bacteria is removed from the moving stage 8 and placed in an incubator for the cultivation of the bacteria.

Similarly to the example described above from the field of molecular evolution, it is possible to carry out a separation of binding events from libraries obtained by combinatorial chemistry, which are supported on polymer beads. The polymer beads pass through a multistep chemical synthesis which results in a molecule library. This is characterised in that a multiplicity of molecules of the same kind is present on the respective bead surface, whereas the types of molecules on different beads differ in pairs. The suspension of beads, like the suspension of bacteria, is mixed with a ligand labelled with a dye and is subsequently washed. Here a dye having a long wavelength such as, for instance, Cy5 is advantageously used for the labelling with dye, in order to decrease the background fluorescence of the beads. The beads are then placed on an agarose surface and analysed by fluorescence spectroscopy in the manner described above. For the process of separating individual beads, the separation actuator used is likewise a glass capillary, the opening of which has a diameter accommodated however to the dimensions of beads of about 100 $\mu$m in diameter. The separation process is likewise carried out by suction of individual beads and subsequent rinsing out on a spatially separated substrate.

What is claimed is:

1. A device for screening molecular libraries based on the binding of fluorescent ligands to library constituents, the device comprising an inverse fluorescence microscope and a moving stage for holding a substrate together with plated-out objects and a first light source for exciting a first fluorescence at a first wavelength and a second light source for exciting a second fluorescence at a second wavelength, the second wavelength being different than the first, wherein, a) a CCD camera measuring the total image or stepwise partial images of the substrate for the identification of a first local fluorescence-intensity of the plated-out objects emitted in response to excitation by said first light source, and a second fluorescence intensity of said plated-out objects in suspension emitted in response to excitation by said second light source, which CCD camera connected to an image calculator for comparing identified fluoresncence intensities to the predetermined selection criteria such that (i) the first fluorescence intensity is above a threshold value, $S_1$, and (ii) the quotient of the first and second fluorescence intensities is above a threshold value $S_2$, and to select one or more of the plated-out objects of the substrate having fluorescence intensities that satisfy the predetermined criteria of (i) and (ii), and for recording the position on the substrate of said selected objects and ascribing to the selected objects location coordinates that have been determined from pixel coordinates in the image measured by the CCD camera and storage of said selected objects' fluorescent image information and their location coordinates;

b) a separation actuator for the transfer of the selected objects is arranged above the moving stage;

c) and the image calculator controls the positioning of the moving stage relative to the separation actuator.

2. The device according to claim 1, wherein the separation actuator comprises a lowerable microcapillary connected to a micromanipulator.

3. The device according to claim 1, wherein the light which excites the first and/or second fluorescence is passed to the substrate across at least one optical waveguide separated from the path of the excitation light.

4. The device according to claim 3, comprising a single optical waveguide, and wherein the first and second light sources emit beams having different wavelengths, the first and second light sources being are enclosed in the single optical waveguide.

5. The device according to claim 1, wherein the fluorescence microscope including the first and second light sources and the separation actuator are incorporated into a climatic chamber, which is cooled to temperatures of between 1° C. and 10° C. by means of a current of air saturated with water vapor.

6. The device of claim 5 wherein the separation actuator comprises a moveable microcapillary.

* * * * *

UNITED STATES PATENT AND TRADEMARK OFFICE
CERTIFICATE OF CORRECTION

PATENT NO. : 6,713,264 B2
DATED : March 30, 2004
INVENTOR(S) : Luttermann et al.

It is certified that error appears in the above-identified patent and that said Letters Patent is hereby corrected as shown below:

Column 10,
Line 24, "camera connected" should read -- camera is connected --
Line 51, "waveguide separated from" should read -- waveguide from --

Signed and Sealed this

Twenty-eighth Day of December, 2004

JON W. DUDAS
*Director of the United States Patent and Trademark Office*